United States Patent [19]

Shikata et al.

[11] Patent Number: 4,661,102

[45] Date of Patent: Apr. 28, 1987

[54] DISPOSABLE DIAPER FEATURING CROTCH TENSIONING MEANS FOR IMPROVED LEAKAGE RESISTANCE AND FIT

[75] Inventors: Hiroaki Shikata; Jerry Turner; Dennis O. Hirotsu; Susan E. Burnett, all of Cincinnati, Ohio

[73] Assignee: The Procter & Gamble Company, Cincinnati, Ohio

[21] Appl. No.: 805,532

[22] Filed: Dec. 3, 1985

[51] Int. Cl.[4] .............................................. A61F 13/16
[52] U.S. Cl. ............................................... 604/385 A
[58] Field of Search .................... 604/385.1, 385.2, 358

[56] References Cited

U.S. PATENT DOCUMENTS

| | | |
|---|---|---|
| 3,860,003 | 1/1975 | Buell . |
| 4,050,462 | 9/1977 | Woon et al. . |
| 4,336,803 | 6/1982 | Repke . |
| 4,430,086 | 2/1984 | Repke ................................. 604/385 |

Primary Examiner—John D. Yasko
Attorney, Agent, or Firm—John M. Pollaro; Fredrick H. Braun; Richard C. Witte

[57] ABSTRACT

A disposable diaper having front and rear waist portions and comprising a liquid permeable topsheet; a liqid impermeable backsheet affixed to the topsheet; an absorbent core interposed between the topsheet and the backsheet; a crotch portion located intermediate the front and rear waist portions; a pair of side flaps; and crotch tensioning means associated with each of the side flaps. The absorbent core has oppositely disposed end portions and a pair of longitudinally disposed side edges therebetween. The crotch tensioning means further comprises one or more elasticized members extending from an attachment area in the crotch portion of the diaper, across the respective side flap, to a location longitudinally outside of the crotch portion. The crotch tensioning means thereby tend to impose outward lateral tension on the crotch portion of the diaper when in use. The attachment areas for such crotch tensioning means are preferably oppositely disposed within the crotch portion of the diaper and are laterally spaced from one another at a width of less than approximately 153 mm. The resulting disposable diaper provides improved aesthetic fit on the wearer and improved containment of voided materials.

15 Claims, 6 Drawing Figures

DISPOSABLE DIAPER FEATURING CROTCH TENSIONING MEANS FOR IMPROVED LEAKAGE RESISTANCE AND FIT

TECHNICAL FIELD

This invention relates to a disposable diaper having elasticized leg openings, and, more particularly, to a disposable diaper having improved leakage resistance and fit as a result of tensioning means located within the crotch portion thereof.

BACKGROUND ART

Disposable diapers are well-known articles of manufacture which are designed to be worn by infants and incontinent persons. Disposable diapers are worn about the lower torso of the user and are intended to absorb and contain voided urine and feces thereby preventing the soiling, wetting, or similar contamination of articles (e.g., clothing, bedding, other persons, etc.) which may come into contact with such diaper in use.

There are numerous executions of disposable diapers available in the industry which generally comprise an absorbent core encased between a liquid permeable user-contacting topsheet and a liquid impermeable backsheet. Additionally, numerous disposable diapers are available in the industry which feature elastic means formed along that portion of the disposable diaper which contacts the wearer's thighs to thereby provide elasticized leg openings for such diaper in use. For example, U.S. Pat. No. 3,860,003, which issued to K. B. Buell on Jan. 14, 1975 discloses an integral disposable diaper which includes opposite, flexible side flaps in the crotch area of the diaper having an elastic member secured to each of such side flaps to provide an elasticized, contractible line through the side flaps, making them compliant and forming effective seals about the wearer's legs. The Buell elastic members are operatively associated with the side flaps so that in a normally unrestrained configuration, the elastic member effectively gathers the side flap material thereabout to provide an elasticized-contractible line through the side flaps adjacent the outer lateral edge thereof. A disposable diaper featuring an elastically constricted crotch section is shown in U.S. Pat. No. 4,050,462, which issued to Woon et al. on Sept. 27, 1977. The Woon et al. diaper comprises a crotch section disposed between two opposite waist sections, with the crotch section being longitudinally constricted by elastic means secured to the backing sheet adajcent each of the side edges of the crotch portion. The elastic means is designed such that when in the non-extended condition, a plurality of gross, transverse rugosities are provided across the width of the crotch section of the diaper. These transverse rugosities thereby reduce the length of the crotch section without reducing the amount of the absorbent material therein, thereby effectively increasing the absorbent capacity per unit area of the diaper in its crotch area.

Other prior art has been aimed at shaping the inner absorbent pad within the disposable diaper to reduce bulk in the crotch area and improve the diaper's fit about the wearer's leg. For example, U.S. Pat. No. 4,336,803, which issued to F. L. Repke on June 29, 1982, concerns a disposable diaper having a shaped absorbent pad which reduces the bulk between the wearer's legs while allegedly maintaining excellent absorptive efficiency of such absorbent pad. Specifically, the Repke shaped absorbent pad is to have a series of indentations formed along its opposite longitudinal edges to provide a short area between one end of the pad and the deepest portion of the indentations, and a long area between the opposite area of the pad wherein a second indentation is formed. The short portion of the absorbent pad is to be positioned in the front of the baby, and the longer portion is to extend between the babies legs and behind the buttocks. Such shape allegedly reduces bulk without negatively affecting abosrptive capacity of the absorbent core. The Repke U.S. Pat. No. 4,336,803 diaper further includes an elastic member along the longitudinal sides of the abosrbent core to provide a tight fit about the baby's legs. Similarly, U.S. Pat. No. 4,430,086, which issued to F. L. Repke on Feb. 7, 1984 discloses a disposable diaper which can include a shaped inner absorbent core; and comprising gathering means having at least two separately extending elastic elements. In particular, the Repke U.S. Pat. No. 4,430,086 diaper includes a pair of elastic strips extending along the opposite longitudinal sides of the diaper which provide two separate and distinct elastic gathers designed to define two separate lines of gasketing around the wearer's legs. The separation of the distinct elastic elements allegedly provides a greater area over which the elastic forces are distributed thereby minimizing the constrictive effect on the wearer's legs.

Despite all the prior work done in this area, there remain problems in optimizing the fit of disposable diapers while at the same time reducing the amount of urine leakage at the legs. Additionally, prior art diapers tend to sag downwardly and bunch inwardly in the crotch area during use, further negatively affecting the diaper's comfort and fit as well as its containment and absorptive functions. Elasticized leg openings tend to migrate into the wearer's leg creases in the crotch area thereby augmenting the sagging/bunching problem and reducing the ability of such prior art diapers to contain voided substances.

DISCLOSURE OF THE INVENTION

It is an object of this invention to obviate the above-described problems.

It is another object of the present invention to provide a disposable diaper which includes crotch tensioning means which tend to impose outward lateral tension on the crotch portion of the diaper when in use thereby improving aesthetic fit and containment characteristics of such diaper.

It is yet another object of the present invention to provide a disposble diaper whose inherent structure tends to direct voided substances directly into an abosrbent core in the diaper thereby avoiding run-off and leakage.

In accordance with one aspect of the present invention, there is provided a disposable diaper having front and rear waist portions, and comprising a liquid permeable topsheet; a liquid impermeable backsheet affixed to the topsheet; an absorbent core interposed between the topsheet and the backsheet; a pair of side flaps adjacent the longitudinal side edges of the absorbent core; and crotch tensioning means associated with each of the side flaps. The disposable diaper is to have a crotch portion located intermediate the front and rear waist portions thereof, and the crotch tensioning means each further comprise one or more elasticized members extending from an attachment area preferably adjacent the longitudinal edge of the absorbent core in the crotch portion, across the respective side flap to a location longitudinally outside of the crotch portion. The attachment areas of such crotch tensioning means are oppositely disposed within the crotch portion of the diaper and laterally spaced from one another at a width of approximately 153 mm or less. In this way, the crotch tensioning means tend to impose outward lateral tension on the crotch portion of the diaper when in use.

BRIEF DESCRIPTION OF THE DRAWINGS

While the specification concludes with claims particularly pointing out and distinctly claiming the present invention, it is believed that the same will be better understood from the following description taken in conjunction with the accompanying drawings in which:

DETAILED DESCRIPTION OF THE INVENTION

Figure 1:
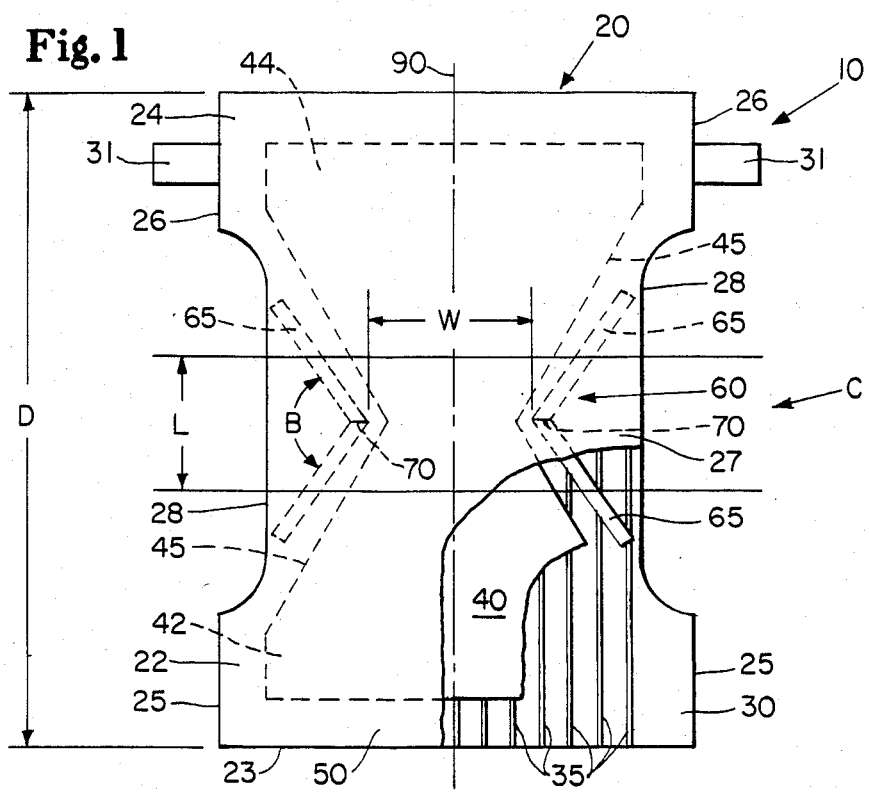
FIG. 1 is a partially cutaway plan view of a disposable diaper of the present invention in an unfolded configuration.

Referring now to the drawings in detail, wherein like numerals indicate the same elements throughout the views, a disposable diaper 10 of the present invention is shown in FIG. 1. As used herein, the term "disposable diaper" refers to a garment generally worn by infants or incontinent persons which is drawn up between the legs and fastened about the waist of the wearer, and which is intended to be discarded after a single use (i.e. it is not intended to be laundered or otherwise restored and reused).

Disposable diaper 10 is illustrated in FIG. 1 in a partially cut-away perspective view illustrating diaper 10 in an unfolded condition. As can be seen in FIG. 1, a preferred diaper 10 basically comprises a liquid permeable topsheet 50, an absorbent core 40, a liquid impermeable backsheet 30, and crotch tensioning means 60. While topsheet 50, absorbent core 40, liquid impermeable backsheet 30, and crotch tensioning means 60 may be assembled in a plethora of well known configurations, a preferred disposable diaper configuration is described generally in U.S. Pat. No. 3,860,003 entitled "Contractible Side Portions for a Disposable Diaper", which issued to K. B. Buell on Jan. 14, 1975, said patent being hereby incorporated herein by reference.

Accordingly, it is preferred that absorbent core 40 be interposed between topsheet 50 and backsheet 30, with backsheet 30 being affixed to topsheet 50. As described and illustrated herein, the topsheet of a disposable diaper of the subject invention is the layer which shall be located adjacent to the wearer in use (i.e., the innermost or user-contacting layer). The manner of locating absorbent core 40 between topsheet 50 and backsheet 30, as well as the manner of affixing backsheet 30 to topsheet 50, are not critical and can be accomplished by a variety of means known in the industry; such as by adhesives, heat sealing, or the like. In a preferred embodiment, a multiplicity of spaced longitudinal adhesive bands 35 are applied along the full length of backsheet 30 generally parallel to the longitudinal center line 90 of diaper 10. The adhesive used for bands 35 is preferably a hot-melt adhesive, but can be any commonly available adhesive which is compatible with the various elements of disposable diaper 10. Longitudinal adhesive bands 35 serve to affix topsheet 50 to backsheet 30 at those locations where such topsheet, backsheet and adhesive bands interface with one another. The extent and location of the areas where topsheet 50, backsheet 30, and longitudinal adhesive bands 35 interface will depend on the spacing between such longitudinal adhesive bands 35, and on the location, shape and size of absorbent core 40 vis-a-vis topsheet 50 and backsheet 30. The number of longitudinal adhesive bands 35, and the spacing therebetween should be designed to sufficiently secure topsheet 50 to backsheet 30 in the area between the diaper periphery 20 and the periphery and longitudinal side edges 45 of absorbent core 40.

A hot-melt adhesive suitable for use as longitudinal adhesive bands 35 is available from the Eastman Chemical Products Company, Kingsport, Tenn., and is marketed under the trade name of Eastobond A-3. Diaper periphery 20 is preferably formed by the boundaries of topsheet 50 and backsheet 30. In this regard, it is preferred that topsheet 50 and backsheet 30 feature substantially identical peripheral shapes and sizes so that their boundaries are in substantial registry with one another thereby forming diaper periphery 20. It will be noted that the described manner of affixing topsheet 50 to backsheet 30 results in topsheet 50 being intermittently attached to backsheet 30 and thereby encasing absorbent core 40 therebetween. It is contemplated that alternative methods of affixing topsheet 50 to backsheet 30 may be equally substituted for the above described procedure; for example, an intermediate member (not shown) may be used to affix topsheet 50 to backsheet 30, similarly encasing absorbent core 40 therewithin.

Disposable diaper 10 is shown as including a first or front waist portion 22 and a second or rear waist portion 24. Front waist portion 22 extends from the front edge 23 of diaper 10 inwardly a predetermined distance toward the center of diaper 10. The rearwardly extending edges 25 of front waist portion 22 intersect with the front edges of the contoured edges 28 of diaper periphery 20. Similarly, the frontwardly extending opposite edges 26 of rear waist portion 24 intersect with the rear edges of contoured edges 28. While the longitudinal length of edges 25 and 26 may vary between particular embodiments of diaper 10, generally such waist portions extend toward the center of the diaper a distance from about $\frac{1}{4}$ to about $\frac{1}{3}$ the overall length of the diaper. Waist portions 22 and 24 comprise those portions of diaper 10 which, in use, encircle the waist of the wearer. On the other hand, crotch portion C is that portion of diaper 10 between front waist portion 22 and rear waist portion 24 which, in use, is positioned between the legs of the wearer. Crotch portion C is illustrated in FIG. 1 as having a longitudinal length L. The remaining portions of diaper 10 situated between waist portions 22 and 24, respectively, and the crotch portion C, cover the front and rear lower torso of the wearer in use.

Absorbent core 40 may be any means which is generally compressible, conformable, non-irritating to the wearer's skin, and which is capable of absorbing and retaining liquids. The absorbent core 40 shown in FIG. 1 is illustrated as comprising a single absorbent layer, however, it is contemplated that a plurality of absorbent layers could be combined and/or laminated to form absorbent core 40. Absorbent core 40 is intended to absorb and contain voided liquid and may be manufactured in a wide variety of sizes and shapes (e.g., rectangular, hourglass, etc.), and from a wide variety of liquid absorbent materials commonly used in disposable diapers (e.g., comminuted wood pulp which is generally referred to as "airfelt", creped cellulose wadding, absorbent foams or sponges, or the like). The total absorbent capacity of absorbent core 40 should be predetermined to be compatible with the designed liquid loading requirements and the intended use of the diposable diaper 10. Accordingly, the size and absorbent capacity of absorbent core 40 may be varied to wearing applications ranging from infants through adults.

Absorbent core 40 is shown in FIG. 1 as featuring a generally hourglass shape, and is intended to be worn by infants ranging in weight from about 12 to about 26 pounds (about 5 kgs. to about 12 kgs.). Absorbent core 40 is preferably a bat of airfelt approximately 15.25 inches (about 387.4 mm) long when measured along longitudinal center line 90, approximately 10 inches (about 254 mm) across the front and rear ends 42 and 44, respectively, and approximately 3.25 inches (about 82.5 mm) across at its narrowest portion in crotch portion C. The absorptive capacity of the airfelt used for absorbent core 40 is preferably designed to be sufficient to absorb and retain from about 8 to about 16 grams of liquid per gram of absorbent material. Accordingly, in a typical diaper 10 designed for use on infants, the airfelt preferably weights from about 20 to about 56 grams. It should be understood, however, that the dimensions, shape and configuration of absorbent core 40 may be varied to accommodate wearers ranging from infants through adults (e.g. the absorbent core may have a varying caliper, or a hydrophilic gradient, or may contain polymeric gelling agents). Additional layers of tissue (not shown) might also be included to improve the tensile strength of absorbent core 40 thereby reducing its tendency to split, lump or ball when wetted; and also to help improve lateral wicking of liquids to provide a more even distribution of liquid voided into the absorbent core 40. Such additional layers are preferably coterminous with absorbent core 40, however, they may have different dimensions and configuration if desired.

Absorbent core 40 is superimposed on backsheet 30 and is preferably affixed thereto by any means well known in the diaper art. For example, absorbent core 40 may be secured to backsheet 30 by a uniform continuous layer of adhesive, by a patterned layer of adhesive, or by a combination of lines and/or spots of adhesive. It is preferred that the longitudinal adhesive bands 35 discussed earlier be used to simultaneously affix absorbent core 40 to backsheet 30, as well as affixing topsheet 50 to backsheet 30.

Backsheet 30 is most preferably impermeable to liquids to thereby prevent liquids absorbed by absorbent core 40 from wetting the undergarments, clothing, bedding, and other objects which a disposable diaper 10 may come into contact with. A preferred material for backsheet 30 is a polyethylene film (e.g. polyethylene film number 8020 available from the Monsanto Chemical Company) of between about 0.0005 and about 0.002 inches (between about 0.012 and about 0.051 mm) in thickness, although other flexible, liquid impermeable materials may equally be utilized. As used herein, the term "flexible" connotes materials which are compliant and which readily conform to the varying shape and contours of the human body. It is preferred that backsheet 30 feature an embossed and/or mat finish to provide a more clothlike appearance and tactile impression. Further, backsheet 30 may be formed with passages which permit the escape of vapors from absorbent core 40 while preventing the passage of liquid therethrough.

As described above, backsheet 30 includes front and rear waist portions 22 and 24, respectively, and oppositely disposed contoured edges 28 thereby forming a modified hourglass shape which extends peripherally outwardly on all sides of absorbent core 40 forming a marginal portion 27 thereabout. Marginal portion 27 thereby preferably extends completely around the periphery of absorbent core 40, forming front and rear endflaps across the distal ends of waist portions 22 and 24, respectively, and oppositely disposed side flaps extending longitudinally on opposite sides of absorbent core 40 between waist portions 22 and 24. The exact width of marginal portion 27 is not critical and may vary in a specific diaper, as illustrated in FIG. 1. As an example, however, the front and rear end flaps formed across the distal ends of waist portions 22 and 24 are typically about 1.5 inches (about 38 mm) or less in length (measured longitudinally on diaper 10).

Topsheet 50 is to be formed of a compliant, relatively soft material which is non-irritating to the wearer's skin and prevents direct contact between absorbent core 40 and the wearer of diaper 10. Additionally, topsheet 50 is to be liquid-permeable to permit voided liquid to readily penetrate therethrough as it is directed to absorbent core 40. Various materials can be used to form topsheet 50, such as natural fibers (e.g., wood or cotton fibers), synthetic fibers (e.g., polyester or polypropylene), a combination of natural and synthetic fibers, or any of the reticulated foams or formed films which are well known in the art. A particularly preferred material for topsheet 50 is a non-woven fabric comprising staple length polypropylene fibers having a denier of about 1.5 (such as Hercules-type 151 polypropylene, available from Hercules, Inc., Wilmington, Delaware). As used herein, the term "staple length fibers" refers to those fibers having a length of about 0.625 inches (about 15.9 mm). It is contemplated that topsheet 50 could be produced by any of a number of manufacturing processes commonly available in the industry. For example, topsheet 50 may be woven, non-woven, spun-bonded, carded, or the like. Preferably, topsheet 50 is carded and thermally bonded by means well known to those skilled in the non-woven fabrics art. A preferred topsheet 50 additionally has a weight of from about 18 to about 25 grams per square yard, a minimum dry tensile strength of at least about 400 grams per centimeter in the machine direction, and a wet tensile strength of at least about 55 grams per centimeter in the cross-machine direction.

Crotch tensioning means 60 are shown as being operatively associated with the longitudinal side flaps of diaper 10, for imposing outward lateral tension on the crotch portion C of diaper 10 when in use. As used herein, the term "associated with" refers to the structural relationship of crotch tensioning means 60 with a particular side flap. In particular, it has been found that crotch tensioning means 60 must comprise one or more elasticized member 65 extending from an attachment area 70 preferably located adjacent the longitudinal edge 45 of absorbent core 40 within crotch portion C of diaper 10. While it is contemplated that a crotch tensioning means 60 could comprise only a single elasticized member 65, it is preferred that at least two relatively oppositely disposed elasticized members 65 be utilized to more evenly provide outward lateral tension to crotch portion C. From attachment area 70, crotch tensioning means 60 extends across the respective side flap to a location which is longitudinally outside of crotch area C. The exact location of attachment area 70 is not critical, however, it has been found that in order to most efficiently impose the desired outward lateral tension on crotch portion C of diaper 10, attachment area 70 is most preferably located adjacent the longitudinal side edge of periphery 45 of absorbent core 40 within crotch portion C. It is, therefore, contemplated that attachment area 70 could be located on absorbent core 40, on the longitudinal side edge of periphery 45 of absorbent core 40, or on the longitudinal side flap adjacent the longitudinal edge of periphery 45 of absorbent core 40 within crotch area C. It has also been found that it is critical that the elasticized members 65 extend from attachment area 70 within crotch portion C to a location longitudinally outside of crotch portion C. Such structural requirement ensures that the desired outward lateral tension will be established by anchoring the source of that tension outside the crotch portion C.

As illustrated in FIG. 1, crotch portion C will have an approximately predetermined length L for a particular embodiment of diaper 10. While the exact length L can vary between various embodiments of diaper 10, it is preferred that crotch portion C be located approximately in the central portion of diaper 10 having its front edge located approximately 35 percent of the overall longitudinal length D of diaper 10 rearwardly from front edge 23 thereof, and having its rear edge located approximately 50 percent of the longitudinal length D of diaper 10 rearwardly of front edge 23. In this regard, it is preferred that crotch portion C be located somewhat forwardly of the physical center of diaper 10 to more closely correspond to the anatomy of the human body. It is also preferred that the narrowest portion of absorbent core 40 be located substantially in the center of crotch portion C.

In order to impose outward lateral tension on crotch portion C, attachment areas 70 are illustrated as located on the respective side flaps of diaper 10 adjacent core periphery 45 of absorbent core 40 within crotch portion C. While attachment areas 70 need not be located adjacent the narrowest portion of absorbent core 40, it is preferred to locate such attachment areas approximate the center of crotch area C in order to more evenly distribute the outward tension thereacross. Similarly, while crotch tensioning means 60 are shown as comprising a pair of oppositely disposed elasticized members 65 radially extending outwardly from attachment points 70, it is contemplated that any number of elasticized members 65 could extend from the respective attachment areas 70 associated with each of the side flaps of diaper 10 to a location longitudinally outside of crotch portion C to establish the desired outward lateral tension thereon. Accordingly, a plurality of elasticized members 65 could radially extend from attachment area 70 to locations outside of crotch portion C. However, it must be remembered that such elasticized members 65 are to impose outward lateral tension on crotch portion C and so must be disposed in radial directions from attachment areas 70 to accomplish that function. As used herein, the term "outward lateral" tension is used to describe the requirement that the resultant tension vector established by the crotch tensioning means in a diaper of the subject invention while in use will have a substantial outward component oriented approximately outwardly normal to the longitudinal center line (e.g., 90) or central axis of such diaper. Therefore, in diaper 10 as shown and described, the tension vectors established by the individual elasticized members 65 would include a component directed outwardly toward the contoured edges 28 thereof substantially perpendicular to center line 90. While orientation of the elasticized members 65 can be altered by varying the included angle B therebetween, it is critical that the resultant tension vectors of such elasticized members include a substantial outward component in order to establish the outward tension on diaper 10.

Elasticized members 65 are illustrated in FIG. 1 as extending radially outwardly from attachment areas 70 thereby forming substantially V-shaped elasticized tensioning means 60. In particular, elasticized members 65 form the vertex of V-shaped tensioning means 60 along single attachment lines 70. This particular V-shape structure has been illustrated only as an example, as it has been found that such elasticized members need not always extend outwardly relative to the longitudinal center line 90 of diaper 10 in order to impose such outward lateral tension. For example, as described in greater detail below with respect to FIG. 2, elasticized members 65 can be substantially collinear relative to one another along a line substantially parallel to center line 90 and still create the desired outward lateral tension crotch portion C. The actual length of the individual elasticized members 65 is not critical except that such members must be sufficiently long to extend from attachment area 70 to a location longitudinally outside of crotch portion C.

In order to impose such outward lateral tension on crotch portion C, crotch tensioning means 60 are affixed to diaper 10 such that they tend to draw such crotch portion C outwardly in use. Thus, when worn, the diaper 10 will have an elasticized longitudinal portion in its crotch portion C. While crotch tensioning means 60 may be affixed to diaper 10 by any of several means well known in the diaper art, a particularly preferred diaper construction incorporating elastic strips is described in detail in the hereinbefore referenced U.S. Pat. No. 3,860,003. In addition, a method and apparatus suitable for manufacturing a disposable diaper having elasticized portions are described in U.S. Pat. No. 4,081,301 entitled "Method and Apparatus for Continuously Attaching Discrete, Stretched Elastic Strands to Predetermined Isolated Portions of Disposable, Absorbent Products" which issued to K. B. Buell on Mar. 28, 1978, such patent being hereby incorporated herein by reference. In this manner, crotch tensioning means 60 are associated with each of the side flaps in an elastically contractible condition so that in a normally unrestrained configuration, elasticized members 65 effectively contract or gather the longitudinal side flaps of diaper 10. In a preferred embodiment, elasticized members 65 are affixed to a portion of backsheet 30 within the respetive side flaps of marginal portion 27 as shown and described. A suitable adhesive for this purpose must be flexible and of sufficient adhesiveness to hold elasticized members 65 to backsheet 30 while the elasticized members are stretched. An adhesive which has been used with satisfactory results for this purpose is manufactured by Century Adhesives Corporation of Columbus, Ohio, and is marketed under the trade name "Century 5227". Crotch tensioning means 60 may be incorporated into diaper 10 in such an elastically contractible condition in any manner known or conceivable by one skilled in the art. For example, elasticized members 65 may be stretched prior to affixation to backsheet 30, or, alternatively, portions of disposable diaper 10 may be contracted (e.g., by pleating) prior to affixation of the unstretched elasticized member thereto.

The material or materials from which elasticized members 65 are formed is not critical and may be any of a number of suitable elastic materials such as natural rubber, or elastomeric films such as ethylene, propylene dimonomer, or polyurethane. Similarly, the width of elasticized members 65 is not critical, and typically may be varied as desired from about 0.0015 inches to about 1.0 inches or more. In addition to adhesives, elasticized members 65 may be affixed to diaper 10 in other manners well known in the art, such as by ultrasonic bonding or heat-sealing. A preferred elasticized member is manufactured of natural rubber (L-1900 Rubber Compound marketed by East Hampton Rubber Thread Co.) having a width of approximately 0.25 inches (about 6.35 mm), a thickness of approximately 0.007 inches (about 0.2 mm), and producing a tensile force of about 100 grams when stretched 100 percent from its relaxed condition.

Diaper 10 is further illustrated as featuring outer fastening means or tape tabs 31 affixed to rear waist portion 24 near the rear edge of diaper 10 for maintaining front waist portion 22 and rear waist portion 24 in an overlapping configuration when diaper 10 is in use. Thus, diaper 10 is fitted to the wearer, and a waist closure is formed thereabout. Outer fastening means 31 must, therefore, be affixed to both the rear and front waist portions in a manner and with sufficient strength to resist forces acting to cause such waist portions to separate during wearing. It is contemplated that any of a variety of alternate fastening means (e.g. velcro strips, patches, buttons, snaps, or the like) could equally be utilized as fastening means 31. In a preferred embodiment, fastening means 31 comprise tape tabs such as the Y-shaped tape as described in U.S. Pat. No. 3,848,594 entitled "Tape Fastening System for Disposable Diaper" which issued to K. B. Buell on Nov. 19, 1974, such patent hereby being incorporated herein by reference.

As illustrated in FIG. 1, it has further been found that in order to impose sufficient outward lateral tension on the crotch portion C of diaper 10, attachment areas 70 are preferably oppositely disposed within crotch portion C and laterally spaced from one another at a width W. It has been determined that width W must be less than or equal to approximately 153 mm on a diaper in order that appreciable amounts of outward lateral tension can be established. In other words, if the innermost points of the oppositely disposed attachment areas 70 of a diaper 10 are laterally spaced from one another at a width of greater than approximately 153 mm, insufficient outward lateral tension is created in the crotch portion C of a diaper 10, and the advantages herein described cannot be achieved. It is contemplated that attachment areas 70 could both be located near the center of crotch portion C along centerline 90, (e.g. width W effectively equal to zero), however, such placement would not be preferred as crotch tensioning means 60 might then tend to precipitate bunching of absorbent core 40 in the crotch area. To avoid such bunching, it is preferred that attachment areas 70 be located adjacent opposite the longitudinal side edges of periphery 45 of absorbent core 40 as shown in FIG. 1.

Figure 2:
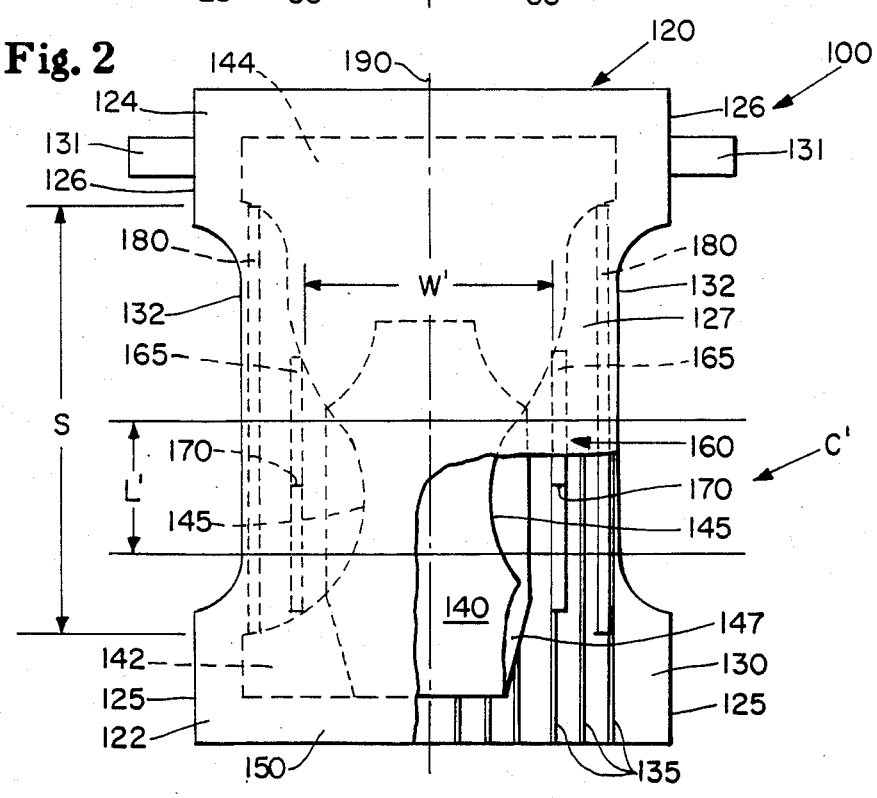
FIG. 2 is a partially cutaway plan view of a preferred embodiment of a disposable diaper of the present invention in unfolded condition.

An alternate embodiment of diaper 10 is shown in FIG. 2, where disposable diaper 100 is illustrated as including a pair of outboard elastics 180, with one outboard elastic being associated with each side flap in an elastically contractible condition and being spaced laterally outward from elasticized members 165 of crotch tensioning means 160. In diaper 100, attachment areas 170 comprise substantially horizontal attachment lines and elasticized members 165 extend radially outwardly from such attachment lines in exactly opposite longitudinal directions such that elasticized members 165 are collinear and extend longitudinally and substantially parallel to the central longitudinal axis 190 of diaper 100. Absorbent core 140 is illustrated as including a second layer of absorbent material 147 which does not conform identically to the shape of absorbent core 140. Such multilayer absorbent core 140 is shown as an example of such a core having a plurality of layers which are not coterminous about their periphery, as mentioned above.

Diaper 100 is illustrated as a more preferred embodiment of the diaper of the subject invention, with the outboard elastics 180 affixed to diaper 100 along both longitudinal side flaps in marginal portion 127, and being designed to draw and hold diaper 100 against the legs of the wearer. Thus, when worn, diaper 100 will have elasticized leg openings in addition to crotch tensioning means. Diaper 100 further illustrates another example of the substantially unlimited shapes and configurations of the absorbent core of the diaper of the subject invention. As described above with regard to diaper 10, crotch tensioning means 160 are designed to impose outward lateral tension on crotch portion C' in use. Unlike crotch tensioning means 60 however, crotch tensioning means 160 are oriented substantially parallel to central axis 190 of diaper 100, having substantially no apparent outward component of the tensioning vectors established by elasticized members 165. However, in use, the wearer's legs will tend to bunch diaper 100 inwardly, putting inward tension on crotch tensioning means 160. Such inward tension is resisted by crotch tensioning means 160, thereby establishing a tension vector having a substantial outward component which tends to impose outward lateral tension on the crotch portion C' of diaper 100. It has been found that to permit the bunching normally created by the wearer's legs to establish such outward lateral tension in diapers having crotch tensioning means 160 oriented substantially parallel to central axis 190, width W' between attachment lines 170 must be at least 60 mm. If width W' is less than approximately 60 mm, insufficient outward lateral tension is provided in crotch portion C' to reduce sagging and bunching therein, as will be described below.

Outboard elastics 180 are preferably spaced a sufficient lateral distance from such crotch tensioning means 160 to enable substantially independent action of such outboard elastics from such crotch tensioning menas. As used herein, the term "independent action" refers to the ability of crotch tensioning means 160 to impose the desired outward lateral tension without relying on or being impaired significantly by tension about the wearer's legs created by outboard elastics 180. Outboard elastics 180 create a snug fit of diaper 100 about the legs of the wearer, while crotch tensioning means 160 provide outward lateral tension on crotch portion C' of diaper 100. As shown in FIG. 2, outboard elastics 180 will preferably have an effective length S which is substantially longer than the required length corresponding crotch tensioning means 160. This is generally true because outboard elastics 180 are designed to provide leg openings which extend around substantially the circumference of the wearer's leg, while, as described above, crotch tensioning means 160 need only extend to locations longitudinally outside of crotch portion C'.

In use, both diapers 10 and 100 perform generally in identical fashions. For example, disposable diaper 100 is generally fitted to the wearer so that diaper 100 conforms to the wearer's waist and legs thereby providing protection against leakage. As generally described above, after diaper 100 is fitted about the waist of the wearer, tape tabs 131 are utilized to affix rear waist portion 124 in an overlapping relationship to front waist portion 122. The extent to which the rear waist portion 124 is overlain on front waist portion 122 will depend on the overall dimensions and shape of diaper 100, and the size of the wearer.

Figure 5:
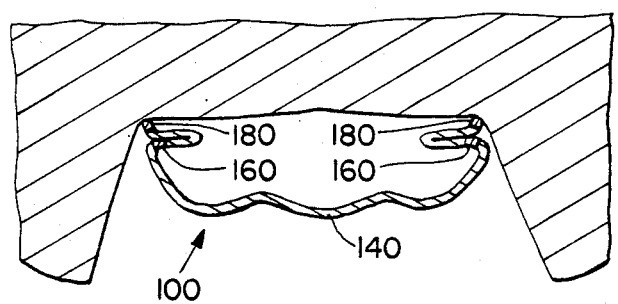
FIG. 5 is a partial cross-sectional schematic view illustrating a disposable diaper made in accordance with the present invention as it would appear between the legs of a user in use.

FIG. 5 illustrates a partial cross-sectional schematic view of the crotch portion C' of diaper 100 as it would generally appear between the legs of a wearer. As described above, elasticized leg openings of diapers tend to migrate into the creases between the wearer's leg in use, as shown by the location of outboard elastics 180 adjacent such leg creases in FIG. 5. However, crotch tensioning means 160 would tend to be located generally below outboard elastics 180 and, as described above, tending to impose outward lateral tension on crotch portion C' of diaper 100, thereby acting to reduce sagging/bunching of diaper 100 between the legs of the wearer and improving aesthetic fit and containment characteristics of the diaper. By imposing outward tension on the crotch portion of diaper 100, crotch tensioning means 160 function to help maintain crotch portion C' nearer to the wearer's body and minimize bunching of diaper 100, thereby facilitating the direction of voided substances directly into absorbent core 140 and greatly reducing liquid run-off and leakage often permitted by otherwise sagging/bunching diapers.

Figure 3:
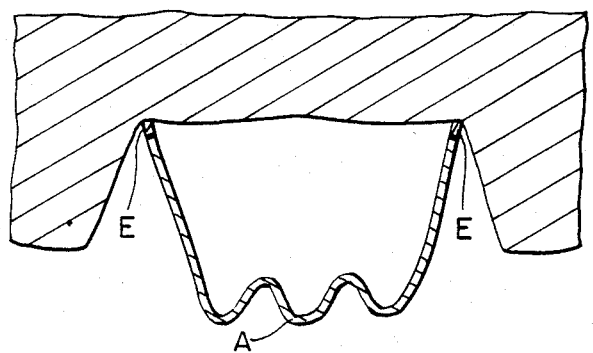
FIG. 3 is a partial cross-sectional schematic view of a prior art disposable diaper featuring elastic leg bands and illustrated as it would appear between the legs of a wearer in use.
Figure 4:
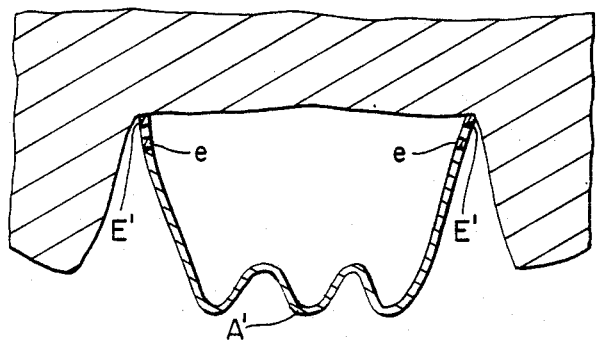
FIG. 4 is a partial cross-section schematic view of a prior art disposable diaper featuring dual elastic leg bands and illustrated as it would appear between the legs of a user in use.

In this regard, FIGS. 3 and 4 illustrate partial cross-sectional schematic views of prior art diaper structures which do not include the unique crotch tensioning means of the present invention. In particular, FIG. 3 illustrates a disposable diaper which includes a single pair of elasticized leg openings E and an absorbent core A. As described, in use the elasticized leg openings E tend to migrate into the wearer's leg creases, and without the crotch tensioning means of the present invention, the absorbent core A and the balance of the diaper located between elasticized leg openings E tends to sag downwardly and bunches inwardly in the crotch area. Such sagging/bunching vitiates the aesthetic fit of such diapers and impairs its ability to contain voided fluids therein. Similarly, FIG. 4 illustrates a prior art diaper having dual elasticized leg openings, illustrated by the inboard elastics e and outboard elastics E'. As can be seen in FIG. 4, the dual elastics similarly tend to migrate into the wearer's leg creases in the crotch area, again permitting substantial sagging/bunching in the diaper crotch area. FIGS. 3 and 4, therefore, illustrate the fact that dual elastics alone do not achieve the outward lateral tension of the subject diapers because they lack the crotch tensioning means of the subject invention. As mentioned, aesthetic fit and containment characteristics of such diapers are greatly compromised as a result of this general tendency to sag or bunch in the crotch area.

In contrast, it can be clearly seen in FIG. 5 that the crotch tensioning means 160 of diaper 100 being oppositely disposed adjacent core 140 and laterally spaced from one another at a predetermined width of between approximately 60 mm and 153 mm, tend to impose outward lateral tension on the crotch portion of diaper 100 thereby greatly reducing sagging and bunching in the crotch portion of such diaper, and thereby improving the aesthetic fit and the ability of the diaper structure to direct voided substances directly into absorbent core 140. It is this tendency to recover from the sagging/bunching forces normally encountered in the crotch area of a diaper during use which distinguishes diapers of the subject invention from others. The result is a disposable diaper having greatly improved leakage resistance and aesthetic fit. It should be noted that while obviously no deformable diaper structure can completely resist inward compression of the crotch area of the diaper between the wearer's legs when the legs are held in close proximity to one another, it is the unique characteristic of the diapers of the subject invention to tend to recover in an outward direction thereby reducing diaper bunching or compression during movement of the wearer's legs and thereby reducing the diaper's tendency to sag.

Figure 6:
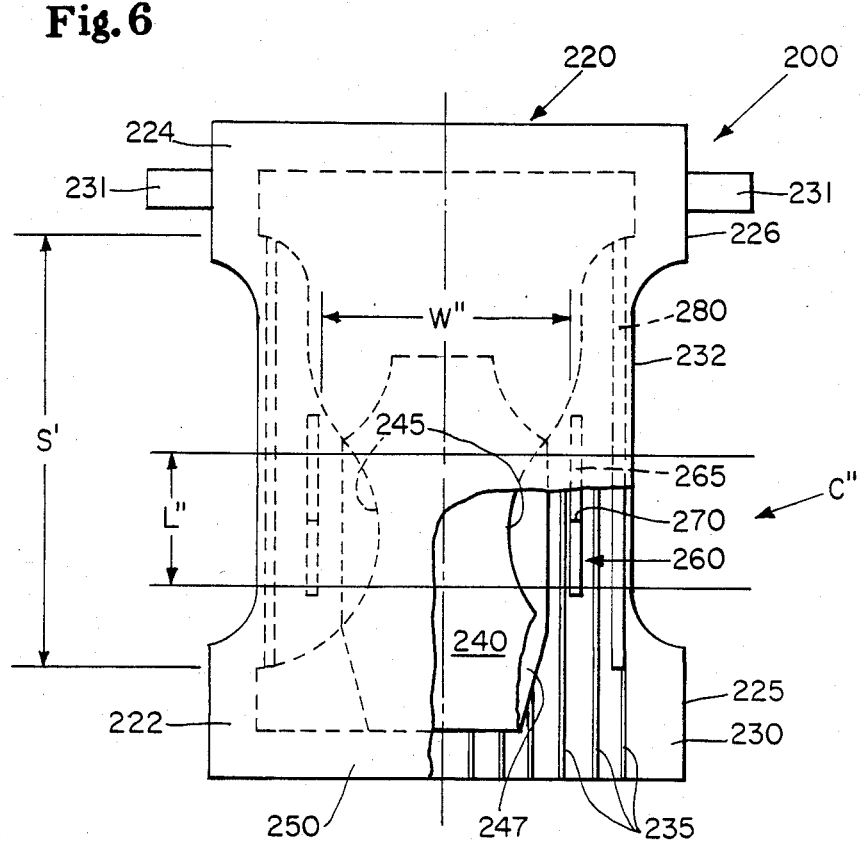
FIG. 6 is a partially cutaway plan view of a third embodiment of a disposable diaper of the present invention.

FIG. 6 illustrates yet another embodiment of a diaper made in accordance with the subject invention. In particular, disposable diaper 200 is illustrated as being substantially identical to diaper 100, described above, except that crotch tensioning means 260 extend radially outwardly from attachment 270 to a location only a short distance longitudinally outside of crotch portion C''. Diaper 200 is illustrated merely to emphasize that crotch tensioning means of the subject invention need only extend from their attachment area within the crotch portion of a diaper to a location longitudinally outside of such crotch portion. In this regard, elements designated in FIG. 6 by numerals having their last two digits the same as the last two digits of numerals shown in FIGS. 1 and 2, respectively, indicate corresponding elements.

Crotch tensioning means 160 of diaper 100 are illustrated in FIG. 2 as having their distal ends adjacent the longitudinal edges of periphery 145 of absorbent core 140. While this arrangement is preferred as providing slightly more outward tension in crotch portion C', it has been found that the shorter crotch tensioning means 260 of diaper 200 can also be utilized to achieve the benefits of the subject invention while minimizing the elastic material necessary to form crotch tensioning means 260.

Having shown and described the preferred embodiment of the present invention, further adaptions of the disposable diaper described herein can be accomplished by appropriate modifications by one of ordinary skill in the art without departing from the scope of the present invention. Accordingly, the scope of the present invention should be considered in terms of the following claims and is understood not to be limited to the details of structure and operation shown and described in the specification and drawings.

What is claimed is:

1. A disposable diaper having front and rear waist portions, said diaper comprising:
   (a) a liquid permeable topsheet;
   (b) a liquid impermeable backsheet, said backsheet being affixed to said topsheet;
   (c) an absorbent core interposed between said topsheet and said backsheet, said absorbent core having oppositely disposed end portions and a pair of longitudinal side edges therebetween;
   (d) a crotch portion located intermediate said front and rear waist portions;
   (e) a pair of side flaps, one side flap being adjacent each of said longitudinal side edges of said absorbent core; and
   (f) crotch tensioning means associated with each of said side flaps for imposing outward lateral tension on the crotch portion of said diaper when in use independent of any tension created by separate elasticized leg openings which may be incorporated, said crotch tensioning means each comprising one or more elasticized members extending from an attachment area in said crotch portion, across the respective side flap to a location longitudinally outside of said crotch portion, said attachment areas being oppositely disposed within said crotch portion and laterally spaced from one another at a distance less than approximately 153 mm to thereby establish said outward lateral tension in use on said crotch portion to reduce sagging and bunching thereof.

2. The disposable diaper of claim 1, wherein said crotch tensioning means each comprise two or more substantially straight elasticized members extending radially outwardly from said attachment areas, said elasticized members extending radially outwardly in relatively opposite longitudinal directions such that their distal ends are located outside said crotch portion.

3. The disposable diaper of claim 2, wherein each attachment area is a single attachment line located adjacent opposite longitudinal edges of said absorbent core, and wherein said elasticized members on each side flap extend radially outwardly from such attachment line to form a substantially V-shaped elasticized tensioning structure, each V-shaped structure having its vertex along said single attachment line with its elasticized members extending radially outwardly in relatively opposite longitudinal directions such that their distal ends are located outside said crotch portion.

4. The disposable diaper of claim 2, wherein each attachment area is a single attachment line located adjacent opposite longitudinal edges of said absorbent core, and wherein said elasticized members on each side flap extend radially outwardly from such attachment line in exactly opposite longitudinal directions such that such elasticized members are collinear and extend longitudinally and substantially parallel to the central longitudinal axis of said diaper.

5. The disposable diaper of claim 4, further comprising a pair of outboard elastics, one outboard elastic being associated with each side flap in an elastically contractible condition, said outboard elastics being spaced laterally outward from said corresponding crotch tensioning means to provide elasticized leg openings for said diaper.

6. A disposable diaper having front and rear waist portions, said diaper comprising:
   (a) a liquid permeable topsheet;
   (b) a liquid impermeable backsheet, said backsheet being affixed to said topsheet;
   (c) an absorbent core interposed between said topsheet and said backsheet, said absorbent core having oppositely disposed end portions and a pair of longitudinal side edges therebetween;
   (d) a crotch portion located intermediate said front and rear waist portions;
   (e) a pair of side flaps, one side being adjacent each of said longitudinal side edges of said absorbent core;
   (f) crotch tensioning means associated with each of said side flaps for imposing outward lateral tension on the crotch portion of said diaper when in use independent of any tension created by separate elasticized leg openings which may be incorporated, said crotch tensioning means each comprising one or more substantially straight elasticized members extending from an attachment area adjacent said longitudinal edge of said absorbent core in said crotch portion, across the respective side flap to a location on said side flap longitudinally outside of said crotch portion, said attachment areas being oppositely disposed within said crotch portion and laterally spaced from one another at a width of less than approximately 153 mm to thereby establish said outward lateral tension in use on said crotch portion to reduce sagging and bunching thereof; and
   (g) a pair of outboard elastics, one outboard elastic being associated with each side flap in an elastically contractible condition, said outboard elastics being spaced laterally outward from said corresponding crotch tensioning means and providing elasticized leg openings for said diaper.

7. The disposable diaper of claim 6, wherein said crotch tensioning means each comprise two or more elasticized members extending radially from said attachment areas, said elasticized members extending outwardly in relatively opposite longitudinal directions such that their distal ends are located outside of said crotch portion.

8. The disposable diaper of claim 7, wherein each attachment area is a single attachment line, and wherein said elasticized members associated with each side flap extend radially from such attachment line to form a substantially V-shaped elasticized structure, each V-shaped structure having its vertex along said single attachment line with its elasticized members extending radially outwardly in relatively opposite longitudinal directions such that their distal ends are located outside of said crotch portion.

9. The disposable diaper of claim 7, wherein each attachment area is a single attachment line, and wherein said elasticized members on each side flap extend radially from such single attachment line in exactly opposite longitudinal directions such that the elasticized members of a crotch tensioning means are collinear and extend longitudinally and substantially parallel to the central longitudinal axis of said diaper.

10. The disposable diaper of claims 8 or 9, wherein said absorbent core has a width which varies intermediate said end portions thereof, said width reaching a minimum within said crotch portion of said diaper.

11. A disposable diaper having front and rear waist portions, said diaper comprising:

(a) a liquid permeable topsheet;

(b) a liquid impermeable backsheet, said backsheet being affixed to said topsheet;

(c) a crotch portion located intermediate said front and rear waist portions;

(d) an absorbent core interposed between said topsheet and said backsheet, said absorbent core having oppositely disposed end portions and a pair of longitudinal side edges therebetween, and having said longitudinal side edges defining a width of said absorbent core, said core width varying intermediate said end portions and reaching a minimum in said crotch portion;

(e) a pair of side flaps, one side flap being adjacent each of said longitudinal side edges of said absorbent core;

(f) crotch tensioning means associated with each of said side flaps for imposing outward lateral tension on the crotch portion of said diaper when in use independent of any tension created by separate elasticized leg openings, said crotch tensioning means each comprising one or more substantially straight elasticized members extending from an attachment area adjacent said longitudinal edge of said absorbent core in said crotch portion, across the respective side flap to a location on said side flap longitudinally outside of said crotch portion, said attachment areas being oppositely disposed within said crotch portion and laterally spaced from one another at a width of less than approximately 153 mm to thereby establish said outward lateral tension in use on said crotch portion to reduce sagging and bunching thereof; and (g) a pair of outboard elastics, one outboard elastic being affixed to each side flap in an elastically contractible condition, said outboard elastics being spaced outward lateral from said corresponding crotch tensioning means to provide elasticized leg openings for said diaper.

12. The disposable diaper of claim 11, wherein each said crotch tensioning means comprises a pair of oppositely disposed, substantially collinear, relatively straight elasticized members being associated with each side flap between said outboard elastic and the respective longitudinal side edge of the absorbent core, said elasticized members extending longitudinally and substantially parallel to the central longitudinal axis of said diaper, and being located adjacent said respective longitudinal side edge, the innermost points of the oppositely disposed attachment areas of said elasticized members being laterally spaced from one another at a distance of less than approximately 153 mm.

13. The disposable diaper of claim 12, wherein said elasticized members of said oppositely disposed attachment areas are laterally spaced from one another at a distance in a range of from about 101 to about 115 mm.

14. The disposable diaper of claims 4, 9, or 12, wherein said oppositely disposed attachment areas are laterally spaced from one another at a minimum distance of at least approximately 60 mm.

15. The disposable diaper of claim 14 wherein said crotch tensioning means each have a predetermined length, and wherein said outboard elastics each have a predetermined length, said predetermined legnth of said outboard elastics being substantially greater than the predetermined length of the corresponding crotch tensioning means.

* * * * *